United States Patent [19]

Saito et al.

[11] Patent Number: 4,952,027

[45] Date of Patent: Aug. 28, 1990

[54] DEVICE FOR MEASURING LIGHT ABSORPTION CHARACTERISTICS OF A THIN FILM SPREAD ON A LIQUID SURFACE, INCLUDING AN OPTICAL DEVICE

[75] Inventors: Kenji Saito, Tokyo; Ken Eguchi, Yokohama; Haruki Kawada, Kawasaki; Yoshinori Tomida, Yokohama; Toshihiko Miyazaki, Tokyo; Yukuo Nishimura, Sagamihara; Takashi Nakagiri, Tokyo, all of Japan

[73] Assignee: Canon Kabushiki Kaisha, Tokyo, Japan

[21] Appl. No.: 296,028

[22] Filed: Jan. 11, 1989

Related U.S. Application Data

[62] Division of Ser. No. 870,419, Jun. 4, 1986, Pat. No. 4,813,763.

[30] Foreign Application Priority Data

| Jun. 5, 1985 | [JP] | Japan | 60-120612 |
| Jun. 5, 1985 | [JP] | Japan | 60-120613 |
| Jun. 5, 1985 | [JP] | Japan | 60-120614 |
| Jun. 5, 1985 | [JP] | Japan | 60-120615 |
| Jun. 7, 1985 | [JP] | Japan | 60-122702 |
| Jun. 7, 1985 | [JP] | Japan | 60-122703 |
| Jun. 7, 1985 | [JP] | Japan | 60-122704 |
| Jun. 8, 1985 | [JP] | Japan | 60-123500 |
| Jun. 8, 1985 | [JP] | Japan | 60-123501 |
| Jun. 8, 1985 | [JP] | Japan | 60-123502 |
| Jun. 8, 1985 | [JP] | Japan | 60-123503 |
| Jun. 8, 1985 | [JP] | Japan | 60-123504 |
| Jul. 8, 1985 | [JP] | Japan | 60-148321 |

[51] Int. Cl.$^5$ .................... G02B 27/14; G01N 21/00; B01J 1/10
[52] U.S. Cl. .................... 350/174; 356/432; 422/186
[58] Field of Search ............ 350/169, 170, 171, 172, 350/173, 174; 356/300, 311, 317, 318, 319, 323, 432, 128, 440, 441; 422/186

[56] References Cited

U.S. PATENT DOCUMENTS

| 4,129,358 | 12/1978 | Wei | 350/173 |
| 4,597,630 | 6/1986 | Brandstetter et al. | 350/170 |
| 4,710,030 | 12/1987 | Tauc et al. | 356/432 |
| 4,790,664 | 12/1988 | Saito et al. | 356/432 |

OTHER PUBLICATIONS

"Photothermal Deflection Spectroscopy and Detection", Applied Optics, Apr. 15, 1981, vol. 20, No. 8, pp. 1333–1344.
"Second Sound Spectroscopy: A New Method for Studying Optical Absorption in Solids", Physics Letters, Mar. 22, 1976, vol. 56A, No. 3, pp. 223–224.

Primary Examiner—Eugene R. Larochi
Assistant Examiner—Ronald M. Kachmarlk
Attorney, Agent, or Firm—Fitzpatrick, Cella, Harper & Scinto

[57] ABSTRACT

A film forming device includes an optical device which has a light source, and a first optical system for projecting light beams split by a light splitting device. The light splitting device and the optical system steadily maintain the intensity center of the light beam projected onto a detecting surface of a light detector at an invariable position without positional fluctuation independently of fluctuation of an emitting angle to a thin film of the light source.

4 Claims, 14 Drawing Sheets

FIG. 1A
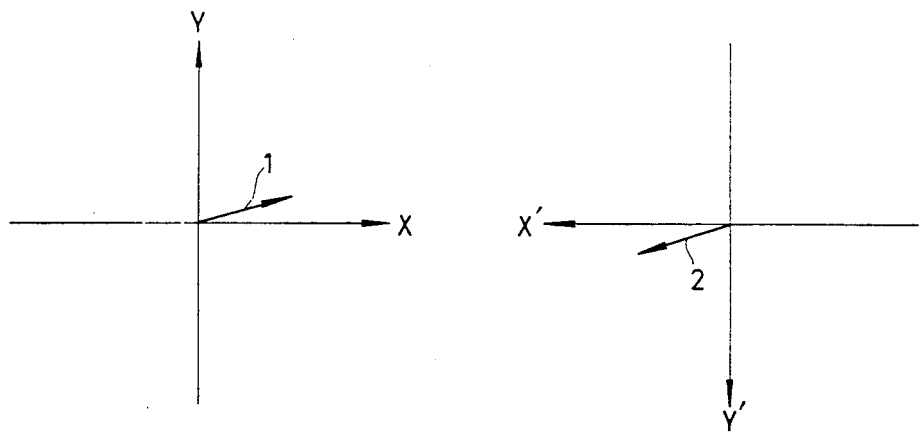
FIG. 1B
FIG. 1C
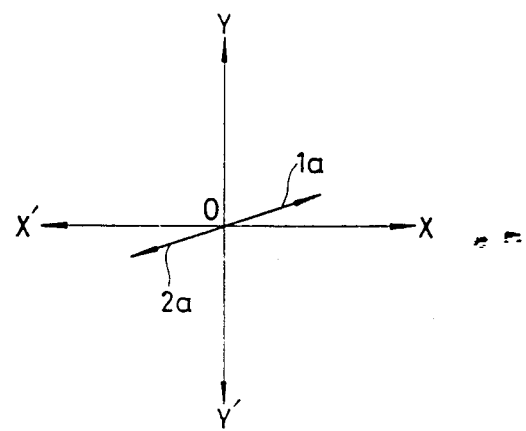

FIG.2
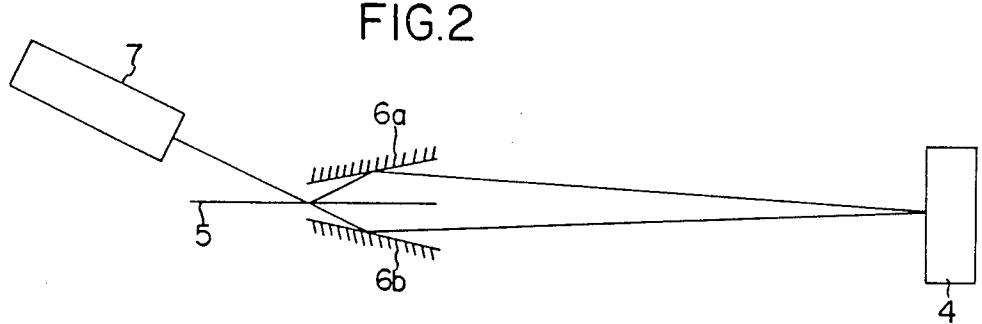
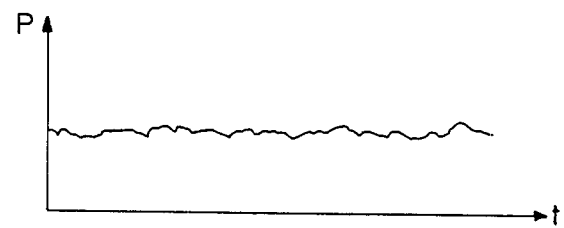
FIG.3A
PRIOR ART
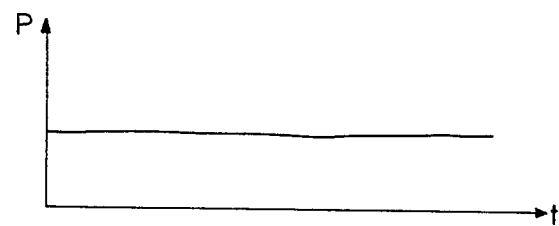
FIG.3B

1

DEVICE FOR MEASURING LIGHT ABSORPTION CHARACTERISTICS OF A THIN FILM SPREAD ON A LIQUID SURFACE, INCLUDING AN OPTICAL DEVICE

This is a division of application Ser. No. 870,419 filed June 4, 1986, now U.S. Pat. No. 4,813,763.

BACKGROUND OF THE INVENTION

1. Field of the Invention

This invention relates to a device and a method for compensating light beam fluctuations in various light beam application devices for recording, display, working, measurement, calculation, etc., and further an optical device equipped with said device, particularly to a light beam fluctuation compensating device and method for effecting compensation so that the intensity center of the irradiating beam will invariably be directed to a predetermined spot and further it relates to an optical device equipped with said device.

2. Related Background Art

In the prior art, as a method for measuring light absorption characteristics of a sample, there is a method of determining light absorption characteristics from transmittance or reflectance. However, when a sample is irradiated with light, scattering of light occurs in addition to transmission and reflection of light, and it becomes important for evaluation of light absorption characteristics to measure directly the absorbed component of light in order to effect further high precision measurement.

As the method for direct measurement of the absorbed component of light, there may be included Photoacoustic Spectroscopy (PAS) which is a measuring method utilizing the phenomenon that the light energy absorbed by a sample is converted intermittently to heat through a radiationless relaxation process when irradiated intermittently with light and the Photothermal Radiometry (PTR).

The PAS method may be classified into the microphone method and the piezoelectric device method according to the detector. In the microphone method, the sample is required to be placed in a sample chamber which is hermetically sealed, while arrangement of the detector and the sample becomes the problem in the piezoelectric device method. Thus, neither method is suitable for measurement of a sample under special environment such as measurement of a thin film spread on a liquid surface. On the other hand, the PTR method employs an IR-ray detector, and therefore has the drawback that it is susceptible to fluctuation in the atmosphere such as water vapor, etc.

On the other hand, also as the method for measuring directly the absorbed component of light, there is a method called Photothermal Deflection Spectroscopy (PDS). The PDS method utilizes the phenomenon that, with heat generation by light absorption of the sample, a temperature distribution is caused in and around the sample to change the refractive index, whereby the light incident thereon is deflected. More specifically, by irradiating exciting light which changes the refractive index by causing a temperature distribution by heat generation at the time of light absorption and a probe light for measuring the deflection caused thereby on the measuring site of a sample, the light absorption characteristics of a sample are measured from the wavelength of the exciting light and the deflection of the probe light. This method can afford setting of a sample and a detection system independently of each other and therefore suitable for measurement at the site or for remote measurement. The PDS method includes the two types of the transverse type and the collinear type depending on arrangement of the exciting light and the probe light, and either method measures the deflection of the probe light corresponding to the exciting light absorption of the sample and position sensitive detector (PSD) is frequently used as the detector.

FIG. 20A is an example of the collinear type, in which the exciting light 111 emitted from the exciting light source 110 is made into an intermittent light beam by the chopper 112 and condensed by the lens 134 to be irradiated on the sample 104. On the other hand, the probe light 106 emitted from the probe light source 105 is permitted to pass through the region of the sample 104 irradiated with the excited light 111 by means of the optical path controller 117 comprising the lens 135 and mirror, etc., and reaches the detector 107, and the deflection when deflected as shown by the broken line is measured. FIG. 20B is an example of the transverse type, which is the same as the collinear type except that the probe light 106 is irradiated in parallel to the surface of the sample 104.

The PDS method can be theoretically dealt with by solving the thermal conduction within the sample, and the deflection measured as the deflection angle $\phi$ is propotional to the excited light intensity, temperature coefficient of refractive index (n/T), the temperature gradient in the region where the probe light passes (T/x), etc. The items proportional to the light absorption coefficient of the sample are included in (T/x). As for (n/T), it can take either positive or negative value depending on the sample, and this means that the angle may be either positive and negative.

FIG. 21 is a longitudinal sectional view showing a structural example of one dimensional PSD. In FIG. 21, the one dimensional PSD constitutes a uniform resistance layer 34 of P layer on the surface of a flat plate silicon 33, provided at both sides with electrodes $X_1$ and $X_2$, having the common electrode 36 provided on the N layer 35 on the back side.

FIG. 22 shows schematically its actuation principle. The charges formed by light corresponding to the incident position of the light Q reach the above resistance layer 34 as photocurrent corresponding to its energy and split in inverse proportion to the distance from the position Q to the take-out electrodes $X_1$, $X_2$ and outputted from the respective electrodes. If the photocurrent by the incident light is defined as $I_L$, the currents $I_{x1}$, $I_{x2}$ become as follows:

$$I_{x1} = I_L \cdot R_{x2}/(R_{x1}+R_{x2})$$

$$I_{x2} = I_L \cdot R_{x2}/(R_{x1}+R_{x2})$$

Further, since the resistance between $X_1$ and $X_2$ maintains uniform distribution, the following respective formulae are valid between the resistance between $X_1$ and $X_2$ and the length L:

$$R_{x1}+R_{x2}=L$$

$$R_{x1}=X$$

$$R_{x2}=L-X$$

For this reason, the signal taken out from the respective electrodes can be represented by L and X as follows:

$$I_{x1} = I_L \cdot (L-X)/L$$

$$I_{x2} = I_L \cdot X/L$$

Thus, informations of incident position of light and light intensity can be obtained at the electrodes of $X_1$ and $X_2$.

Further, by calculating a ratio of the difference between $I_{x1}$ and $I_{x2}$ relative to the sum thereof and defining it as the position signal P, the following formula can be obtained:

$$P = \frac{I_{x1} - I_{x2}}{I_{x1} + I_{x2}} = \frac{L - 2X}{L}$$

Corresponding to x=0 to L, the position signals irrelevant to the light intensity change can be continuously obtained as follows:

$$X = 0 \quad , \quad P = 1$$
$$X = 1/2 \quad , \quad P = 0$$
$$X = L \quad , \quad P = -1$$

The above description concerns the one-dimensional case, and the two-dimensional position detector may be also considered similarly and the position signals can be determined from the block diagram of the actuation circuit shown in FIG. 23.

Here, from the actuation principle of PSD, when there are light incidence of two points or more the position signals weighted in proportion to the respective light intensities can be obtained. Also, in the case when the light flux is expanded, the position signal as the center of gravity of light intensity can be obtained. The center of gravity of light intensity, or center of intensity distribution, of the light beams, is defined as the point where the integral values of intensity of the distributed light become equal in all directions from this point.

However, when the PDS method as described above is applied as such for measurement of a thin film spread on the liquid surface, there is the inconvenience caused by the fact that the thin film of the sample is extremely thin. That is, in measurement using such PSD, the fluctuation in emission angle of the light source itself has a great effect on the measurement precision. Particularly, in measurement by use of gas laser, it has been impossible to perform positional detection at high precision, and it has been difficult to obtain desired light absorption characteristics.

FIG. 24 is a schematic illustration showing one example of the light irradiation device of the prior art. In FIG. 24, the light beam which is emitted from the light source 101 and reaches the target 103 through the lens 102 takes the pathway along the course 104 shown by the solid line or the course 105 depending on the fluctuation in the emitted direction of the light source 101, whereby the positional deviation occurs at the target irradiated position.

FIG. 25A shows fluctuation with time of the positional deviation of light beam, in which the axis of ordinate indicates the positional deviation W and the axis of abscissa the time t. In the Figure, the solid line indicates the position where the intensity of the light beam is at the peak, the dotted line the light beam width., and the positional deviation W is fluctuated randomly with time so that the average value over a long time becomes 0.

FIG. 25B is the results of optical information recording carried out in spots by condensing the above light beam showing the recorded pattern when recording was effected while deviating linearly the position X. As is apparent in this Figure, this shows the problem that the positional precision of the record is lowered by recording of the pattern, which is to be recorded linearly on the X axis, at the position corresponding to the positional deviation W.

FIG. 25C is a graph showing a trace line when laser minute working is performed with the same light beam. This shows the problem that the working line which should be drawn as a straight line on the X axis becomes wavy due to the beam fluctuation.

Such problems can be solved by stabilization of the spot center position, if a long irradiation time is scheduled and measurement is awaited before the light beam settles at the average position. However, such a solution will take too long time and therefore not suitable for high speed recording or working.

SUMMARY OF THE INVENTION

The present invention has been accomplished in view of such problems and it is intended to provide a high precision light beam fluctuation compensating device and method, which can compensate the positional deviation of light beam by fluctuation with time of light source, thereby fixing the center of the irradiated beam intensity at a predetermined position.

Further, the present invention is intended to provide an optical device capable of measuring the light absorption characteristics not only of a solid sample but also of a sample which is very thin and under a special environment such as the thin film spread on the liquid surface by cancelling the influence of fluctuation of the light source itself and enhancing the measurement precision to the limit of resolving power of PSD. The above objects can be accomplished by the present invention as defined below.

According to an aspect of the present invention, there is provided a light beam fluctuation compensating device, comprising a light source, a first optical system for splitting a light beam emitted from said light source into two light beams and a second optical system for irradiating the two light beams split by said first optical system onto a target.

According to another aspect of the present invention, there is provided a light beam fluctuation compensating device, comprising a light source, a first optical system for splitting the light beam emitted from said light source into two light beams, a second optical system for fluctuating either one of the two light beams split by said first optical system relative to a light beam fluctuation in the longitudinal direction in the direction opposite thereto and a third optical system for irradiating said two light beams on a target.

According to still another aspect of the present invention, there is provided a light beam fluctuation compensating device, comprising a light source, a first optical system for splitting the light beam emitted from said light source into two light beams and a second optical system for fluctuating either one of the two light beams split by said optical system relative to the light beam fluctuation in the longitudinal direction in the direction opposite thereto, the two light beams having passed through said first and second optical systems being irradiated as the two light beams close to each other by a third optical system on the target.

According to a further aspect of the present invention, there is provided a light beam fluctuation compensating method, which comprises splitting a light beam emitted from a light source into at least two light beams, and irradiating these light beams within a predetermined region of a target by use of optical systems which make the vector sum of fluctuation of the respective light beams caused by momentary fluctuations in position and emission angle of said light source invariably zero value.

According to a still further aspect of the present invention, there is provided an optical device, comprising excitation light source for emitting exciting light, a light intensity modulator which modulates intensity of the exciting light emitted before the measuring site of a sample, a probe light source for emitting a probe light, a light splitting means for splitting the emitted probe light into two light beams, a means for converting said two split beams relative to the fluctuation of the probe light caused by fluctuation of the probe light source into the two beams of which directional components to be compensated become symmetric to each other, an optical system for leading those beams to said measuring site or the vicinity thereof, and a light position detector for receiving light beams.

According to a still further aspect of the present invention, there is provided an optical device, comprising an excitation light source for emitting an exciting light, a light intensity modulator which modulates intensity of the exciting light emitted before the measuring site of a sample, a probe light source for emitting a probe light, a splitting means for splitting the probe light emitted into two light beams, an optical system for reversing the path of at least one of the light beams being split in the longitudinal direction, a means for converting the light beam having passed through said optical system and the other light beam relative to the fluctuation of light beam caused by fluctuation of said probe light source into the two light beams of which the directional components to be compensated are symmetric to each other, an optical system for leading those light beams to said measuring site or the vicinity thereof, and a light position detector for receiving light beams.

BRIEF DESCRIPTION OF THE DRAWINGS

FIGS. 1A, 1B and 1C, and FIG. 2 are diagrams for illustration of the principle of the light beam fluctuation compensating method of the present invention;

FIGS. 3A and 3B are graphs showing comparison of the results of light beam fluctuation measurement according to the prior art and the present invention;

DETAILED DESCRIPTION OF THE PREFERRED EMBODIMENTS

Figure 4A:
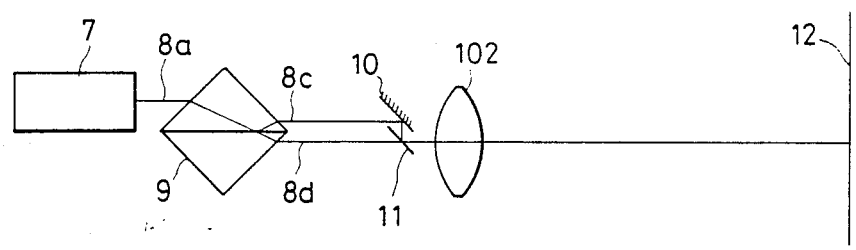
FIGS. 4A, 4B, 5A, 5B, 5C and 6 are schematic illustrations of respective embodiments of the light beam fluctuation compensating device of the present invention.

FIG. 1 shows coordinate diagrams for explanation of the principle of the compensating method according to the present invention. FIG. 1A shows X-Y coordinate axes crossed at right angles to each other on a plane perpendicular to the average emitting direction of the light beams emitted from a light source, the quantity of deflection of emitted light being indicated by the arrowhead 1. Suppose that the above coordinate axes are reversed by a given optical system, then their projections become as indicated by X'- Y' in FIG. 1B, with the reflected amount of emitted light becoming also as shown by the arrowhead 2. When the light beams reversed to each other are irradiated on a target irradiation surface, their coordinates become symmetric (1a, 2a) relative to the original point 0 as shown in FIG. 1C and if the both light beam intensities are equal to each other, the gravitational center of the light beam always coincides with the origin. Accordingly, by use of an optical system satisfying the above conditions, even if there may occur a positional fluctuation in light source, it can be compensated without influence of the intensity center of the irradiated beam.

FIG. 2 is a schematic illustration of the basic constitution for verifying the light beam fluctuation compensating method according to the present invention. The team from a He-Ne light source 7 is split in amplitude by a half mirror 5, and the split light beams are irradiated respectively from mirrors 6a and 6b on a light position detector 4 to record fluctuation of the light source 7. FIGS. 3A and 3B are graphs of the positional deviation of the light beam in accordance with the above constitution, the ordinate axis indicating the detected position P of the light beam and the abscissa axis indicating time t. In FIG. 2, when the light beam is irradiated directly on the light position detector 4 without passing through the optical system comprising the half mirror and mirrors 6a and 6b, the fluctuation is recorded as shown in FIG. 3A, while when compensated according to the present invention, it can be appreciated that the light source fluctuation is removed as shown in FIG. 3B.

Now, the embodiments of the present invention are described in conjunction with the drawings.

FIG. 4A is a schematic illustration of an embodiment of the light beam fluctuation compensating device practicing the present invention. In this Figure, the light beam 8a emitted from the light source 7 is split by a beam splitter 9 into the two light beams 8c and 8d and thereafter become the two light beams close to each other when subjected to a mirror 10 and a half mirror 11 and irradiated on the target surface 12.

Figure 4B:
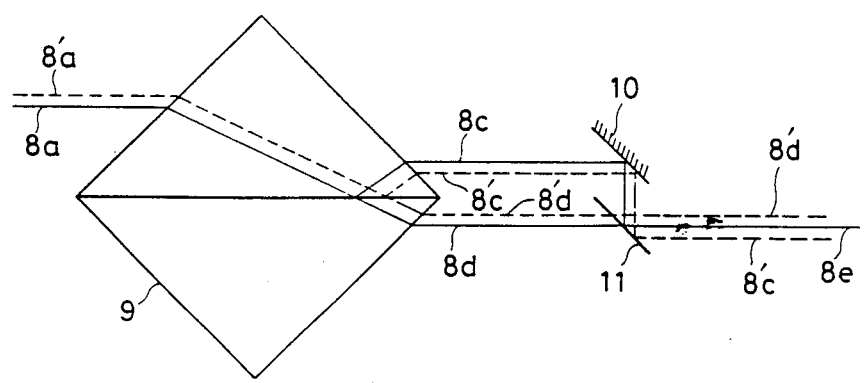

FIG. 4B is an enlarged view of the above split portions of the light beam. Suppose that the light beam 8a is deviated to the position of the light beam 8a' by fluctuation of light source, and the light beam to be irradiated on the target surface is split into the two beams 8c' and 8d' and these two beams are fluctuated symmetrically with the original position of the light beam 8e as the center. Accordingly, they are fluctuated respectively in the directions symmetric to each other with the irradiated point when there is no fluctuation of light source fluctuation can be compensated as explained with respect to the principle of the present invention.

Figure 5A:
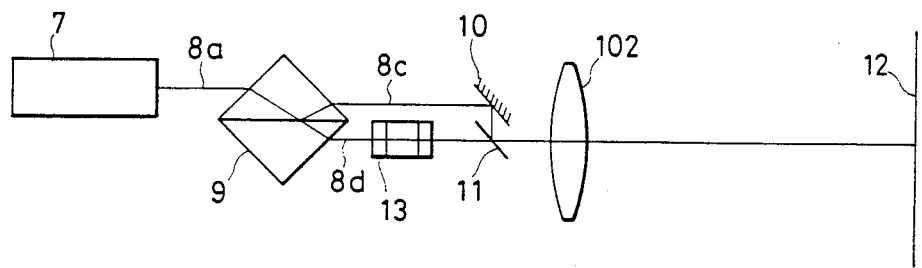

FIG. 5A illustrates schematically another embodiment of the present invention. The constitution in FIG. 5A is substantially the same as the embodiment in FIG. 4A, except that one of the beams 8d split by the beam splitter 9 is additionally made to pass through an image rotator before reaching the half mirror 11. The image rotator 13 reverses the passing position of the light beam in the direction perpendicular to the splitting direction of the beam splitter 9, and it may be in either optical path of the optical beam 8c or 8d.

Figure 5B:
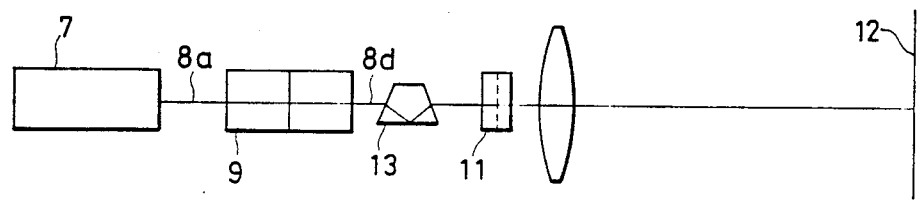
Figure 5C:
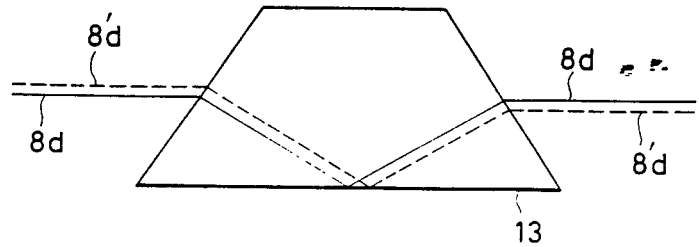

FIG. 5B is a schematic illustration of the side view of the optical path of FIG. 5A, showing particularly the optical path of the optical beam passing through the image rotator 13 of the optical beams split by the beam splitter 9. The light fluctuation component along the splitting direction of the beam splitter can be cancelled by the principle explained with reference to FIG. 4B, but the light source fluctuating component in the direction perpendicular thereto is not cancelled by the beam splitter 9 as is apparent from FIG. 5B. Accordingly, by utilizing reversal of the passing position of the light beam by the image rotator 13 as shown in the partial enlarged view of FIG. 5C, the fluctuating direction of the fluctuated light beam 8d' is reversed to compensate for the deviation based on the principle of the present invention. As a result, by synthesis of the both components (vector components) the deviation in the light beam can be compensated (vector sum is 0) according to the constitution of FIG. 5A even if light source fluctuation may occur in any direction.

Figure 6:
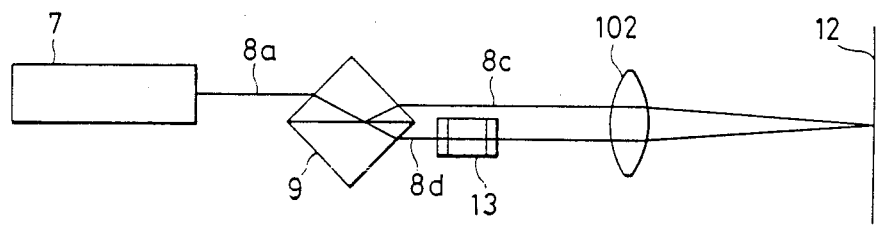

FIG. 6 is a schematic illustration of still another embodiment of the present invention. The light beam 8a emitted from the light source 7 is split into two light beams by the beam splitter 9, while one of them passes through the image rotator 13, both of 8c and 8d are condensed by a lens 102 to be irradiated on the target surface 12. Only difference from FIG. 5A is that the light beams are not condensed by a combination of a mirror and a half mirror, but condensed by a lens and fluctuation compensation of light beam is made possible by an optical system which forms light beams mutually reversed in the two directions perpendicular to each other.

Figure 7A:
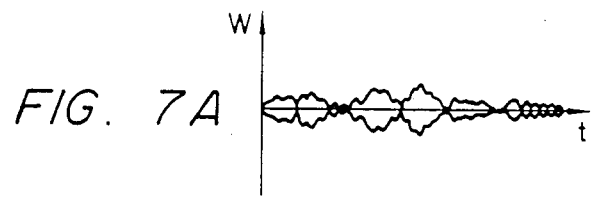
FIGS. 7A, 7B and 7C show fluctuation graphs of the light beam in the present invention.
Figure 7B:
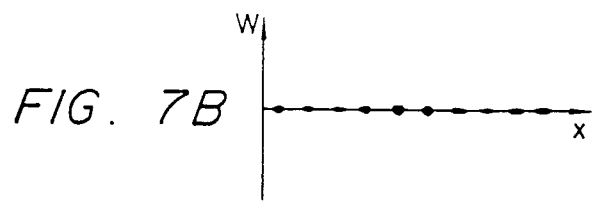
Figure 7C:
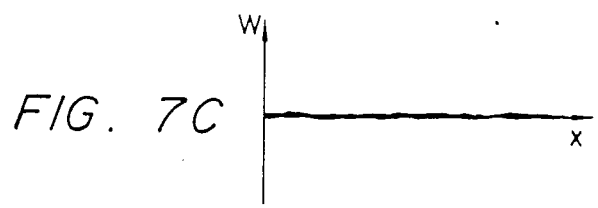
Figure 25A:
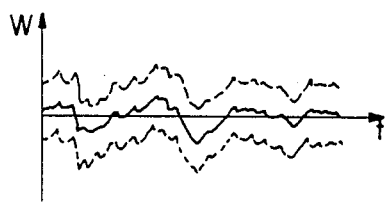
FIGS. 25A, 25B and 25C the fluctuation of the light beam in the prior art device.
Figure 25B:
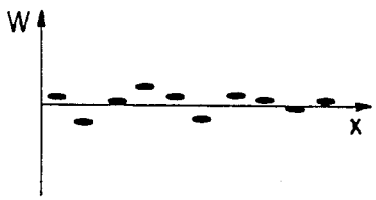
Figure 25C:
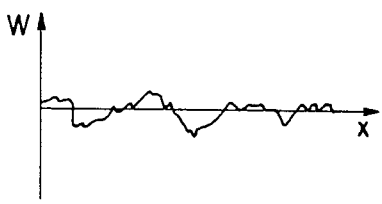

By means of the above compensating device, the positional deviation at the target surface can be compensated as shown in FIG. 7. That is, FIGS. 7A, 7B and 7C are graphs corresponding to the prior art example shown in FIG. 25. The flexed line in FIG. 7A indicates the intensity peak positions of the respective light beams which are symmetric with respect to the average position of W=0 and therefore the intensity center of the light beams is constantly at W=0.

FIG. 7B shows the case in which spot-like optical information was recorded linearly by application of the above compensating device and the center position of the respective spots are positioned on the straight line, thus recording being with good precision. FIG. 7C shows the case when a straight line was drawn in laser minute working, and it can be seen that disturbance of the worked line has significantly decreased as compared with the case of FIG. 25 where no compensation has been done.

Figure 8:
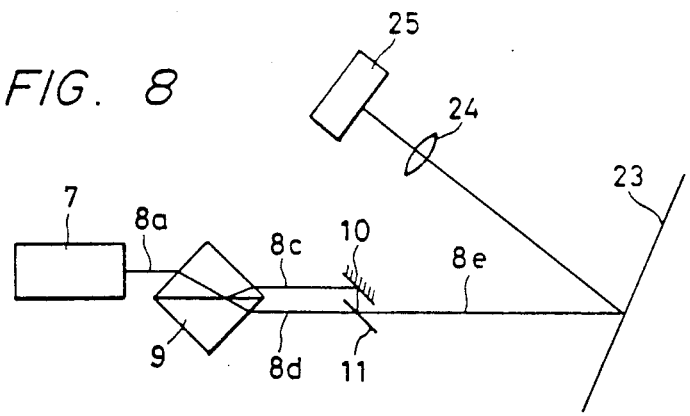
FIGS. 8, 9 and 10 are schematic illustrations of the optical device of the present invention, particularly a deflection-angle displacement measuring device.

FIG. 8 is a schematic illustration showing an embodiment of the optical beam fluctuation compensating device according to the present invention when applied to an angle or displacement measuring device. In FIG. 8, the measuring device measures rotation or movement within the plane of the material 23 to be tested by focusing the light beam 8a emitted from the light source 7 reflected against the material 23 to be tested by the lens 24 on the detecting surface of PSD 25.

Figure 9:
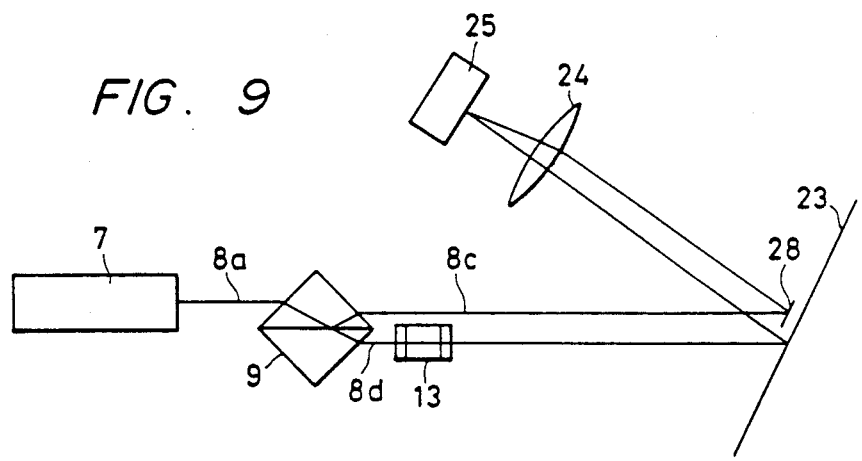

FIG. 9 is a schematic illustration showing another example of an angle or displacement measuring device according to the present invention. In this embodiment, a reference plane 28 is newly provided, one of the optical beams split by the beam splitter 9 is reflected against the reference plane 28 and the other beam 8d against the material to be tested 23, respectively, and both beams are condensed by a lens 24 to be irradiated on the light receiving surface of PSD 25. Also in this case, similarly as in the foregoing embodiment, the two light beams become reversed to each other on PSD, whereby the influence by fluctuation of light source can be cancelled.

The image rotator may be placed in either of the optical paths for the light beams split by the beam splitter. Also, the angle at which the light beam is incident onto the material to be tested may be set as desired.

Figure 10:
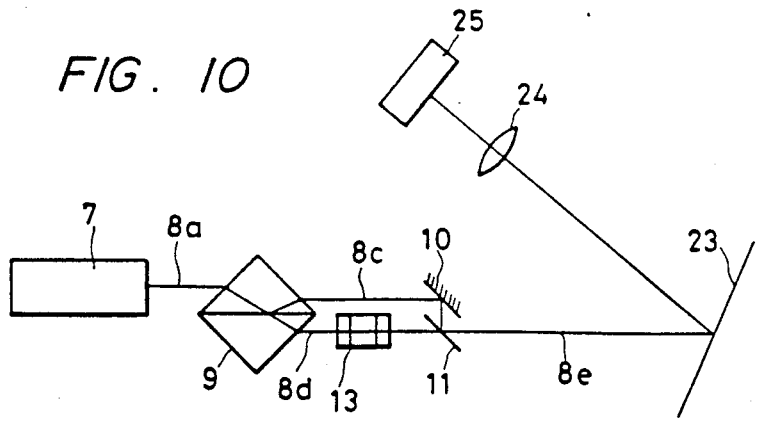

FIG. 10 shows an embodiment in which an image rotator 13 is arranged between the beam splitter 9 and the half mirror 11, with other constitutions being entirely the same as in FIG. 8.

Figure 11:
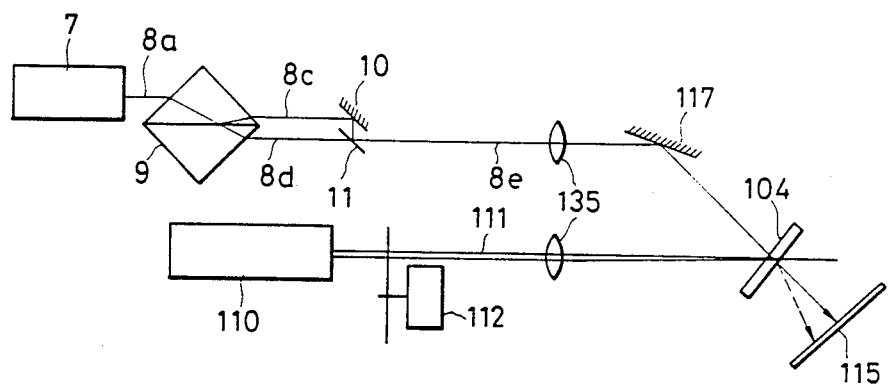
FIGS. 11–15 are schematic illustrations of other embodiments of the present invention, namely optical property measuring device.

FIG. 11 is a schematic illustration showing an embodiment of the optical device in which the light beam fluctuation compensating device of the present invention is applied to a device for measuring optical physical properties. This embodiment is intended to measure the deflection in the longitudinal direction in the figure of the probe light of a sample to be tested by a longitudinal direction type PDS by one dimensional PSD.

The exciting light 111 emitted from the excitation light source 110 is modulated to intermittent light by the chopper 112 and irradiated by focusing through the lens 134 on the sample 104. On the other hand, the beam light 8a emitted from the probe light source 7 is split into the two light beams 8c and 8d by the beam splitter 9 and made into the two light beams close to each other by the mirror 10 and the half mirror 11, thereafter are passed through the exciting light irradiation region of the above mentioned sample 104 by the lens 135 and the optical path controller 117 to be deflected in the longitudinal direction shown by the broken line in the figure in the deflected amount corresponding to the absorption of the exciting light by the sample, and detected on the PSD receiving surface 115 of the light position detector. In this case, even if the beam of the probe light may be fluctuated in minute amount by fluctuation of the probe light source 7, as described above, at the PSD light receiving surface 115 reached via the optical path controller 117 the beams are shifted respectively in the directions symmetric to each other with the position corresponding to the deflected amount by absorption of the sample in the case of no light source fluctuation as the center, whereby the output becomes the constant value corresponding to the absorption of the sample from the measurement principle of PSD, thus cancelling the influence of fluctuation of the probe light source.

Figure 12:
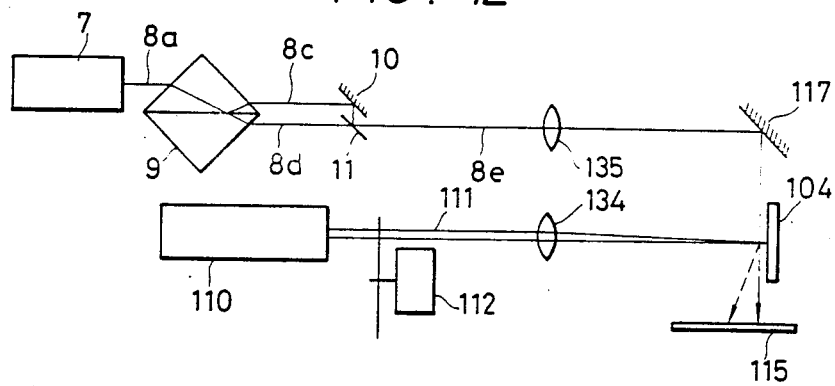

FIG. 12 is a schematic illustration of a second embodiment of the device for measuring optical properties according to the present invention. This embodiment shows one example of the method for measuring optical properties by a transverse type PDS, and it is the same as the embodiment shown in FIG. 11 with respect to the functions of the respective portions except that the irradiation angle of the excitation light and the probe light are those for the transverse type, and it is possible to cancel the influence of fluctuation of the probe light source.

Figure 13:
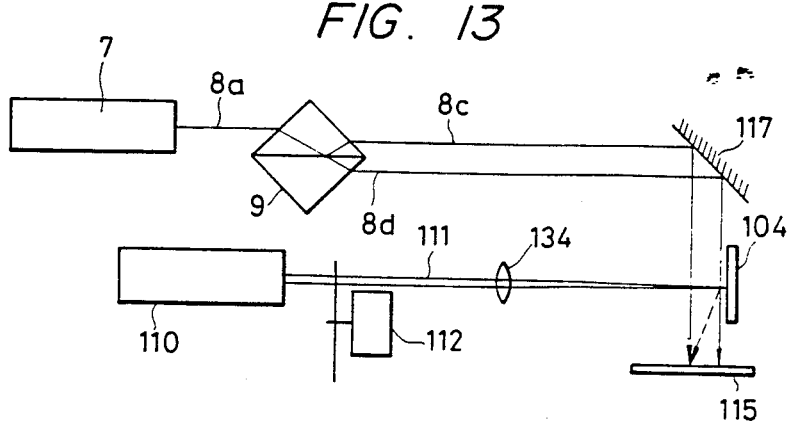

FIG. 13 is a schematic illustration of a third embodiment of the device for measuring optical properties according to the present invention, showing one example according to the transverse type PDS. According to this embodiment, the light beam from the probe light source 7 is split into two beam lights by the beam splitter 9, and thereafter one of the beam lights 8c is permitted to pass through the reference region separate from the region to be measured and finally irradiated on the same PSD light receiving surface 115. Also in this case, according to the measurement principle of PSD, the output becomes the constant value representing the center between the reference probe light position under measuring probe light position corresponding to absorption of sample, whereby the influence of the fluctuation of light source for probe can be cancelled.

Figure 14:
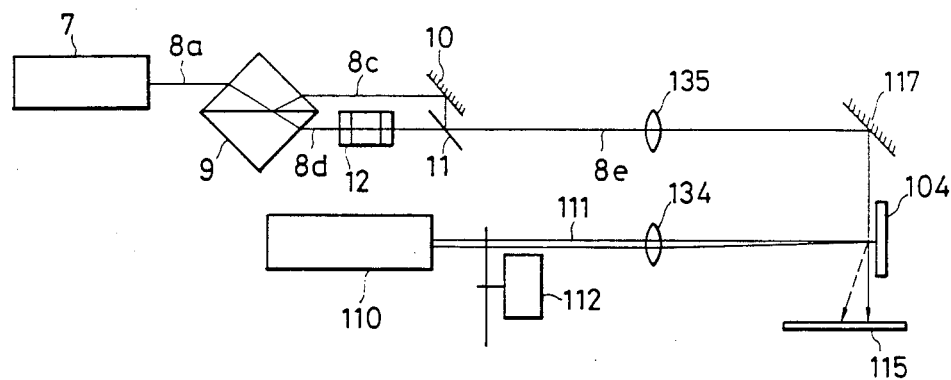

FIG. 14 is a schematic illustration of a fourth embodiment of the device for measuring optical properties according to the present invention, showing one example according to the transverse type PDS. This embodiment shows the case of measuring the deflection in any direction of the probe light by the sample to be detected 104 according to the two-dimensional PSD. By arrangement of an image rotator 12 between the beam splitter 9 and the half mirror 11, one of the probe light beams 8d split by the beam splitter 9 is reversed in the upper and lower passing positions in the direction perpendicular to the splitting direction by the beam splitter 9. Other constitutions are entirely the same as FIG. 12.

Figure 15:
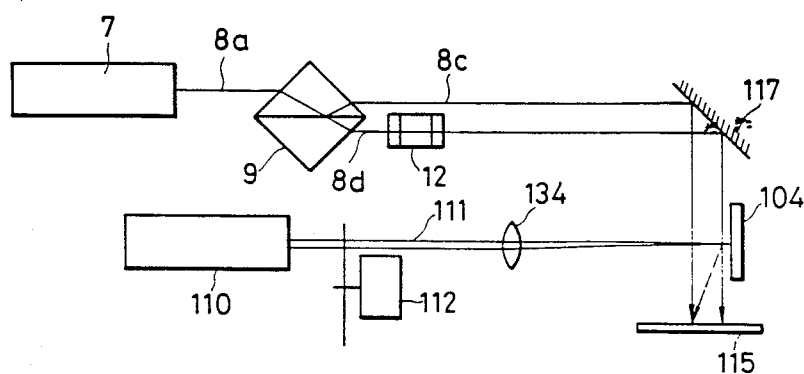

FIG. 15 is a schematic illustration of a fifth embodiment of the device for measuring optical properties according to the present invention, showing an example according to the transverse type PSD.

This embodiment measures the deflection of the probe light in any direction by the sample to be detected 104 by the two dimensional PSD using beam light for reference. After the beam light 8a from the probe light source 7 is split into two beams by the beam splitter 9, one of the beams 8c is permitted to pass through the reference region separate from the region to be measured, and the other beam light 8d for measurement is permitted to pass through the region to be measured, and both beams are irradiated finally on the same PSD light receiving surface 115. Also, in this case, according to the measuring principle of PSD, the output becomes the constant value representing the center between the reference probe light position and the measuring probe light position corresponding to absorption of sample, whereby the influence by fluctuation of light source for probe can be cancelled. The image rotator 12 may be placed in either of the optical paths for the probe lights 8c and 8d split into the two beams by the beam splitter 9.

In the following, there is shown an example in which the light beam fluctuation compensating device of the present invention is applied to a device for forming a monomolecular film (LB film).

Figure 16:
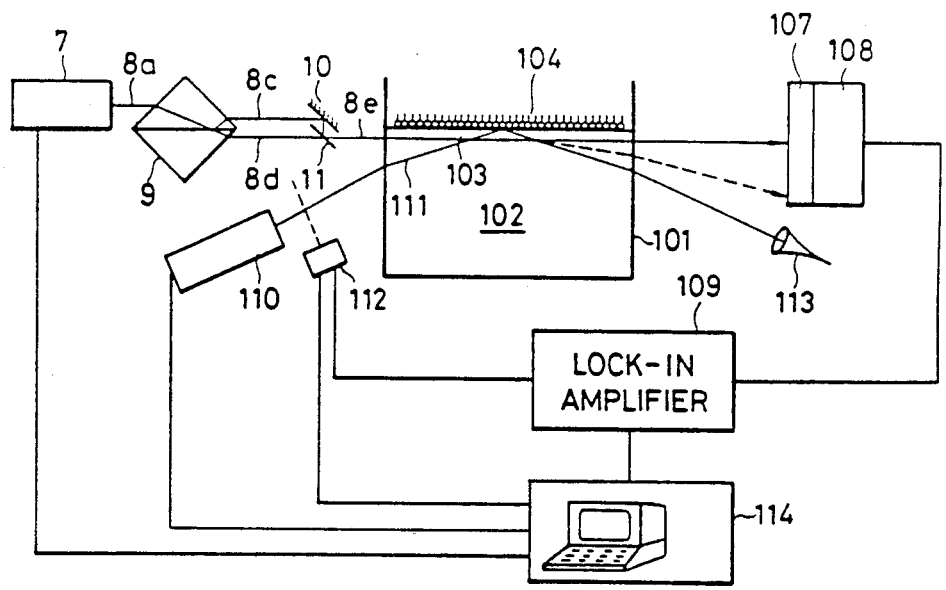
FIGS. 16, 17, 18A, 18B, 18C, 19A, 19B, 19C and 19D are schematic illustrations of other embodiments of the present invention, namely thin film forming devices.

FIG. 16 is a schematic illustration of a first embodiment of the film forming device according to the present invention. This embodiment concerns the case of measuring the deflection of probe light in the longitudinal direction in the drawing by one-dimensional PSD.

In FIG. 16, 101 is a liquid tank, 102 is a liquid, and on the liquid surface 103 of the liquid 102 a thin film 104 for a sample is spread. The thin film 104 shown in the Figure represents schematically a monomolecular film. There is also provided a probe light source 7 beside the liquid tank 101. The light beam 8a emitted from the probe light source 7 is split into the two light beam 8c and 8d by the beam splitter 9, recombined into one light beam 8e by the mirror 10 and the half mirror 11 and irradiated directly beneath the liquid surface 103 in parallel to the liquid surface 103. Also, at the position opposite to the probe light source 7 with a liquid tank 101 interposed therebetween, there is provided a light position detector 107 for detecting the position of the probe light 8e delivered. The signal of this light position detector 107 is sent through the driver 108 to the lock-in amplifier 109.

On the other hand, slightly below the probe light source 7, an excitation light source 110 is provided. This excitation light source 110 irradiates the exciting light 111 from the liquid side 102 toward the measuring site of the thin film 104 at an angle which can afford total reflection against the liquid surface 103 at which the thin film 104 is spread. At the position along the optical path of the exciting light 111 there is provided a chopper 112 for irradiating the exciting light 111 as intermittent light. Also, at the position where the exciting light 111 irradiated from the excitation light source 110 and totally reflected at the liquid surface 103 emits from the liquid tank 101 an absorber 113 for absorbing the exciting light 111 is provided.

The chopper 112 is connected to the rock-in amplifier 109 so that the signal from the detector 107 can be detected synchronously with the signal indicating the intermittent state of the exciting light 111 sent from the chopper 112 as the reference signal. The probe light source 7, the excitation light source 110, the chopper 112 and the lock-in amplifier 109 are connected to the measurement controller 114, respectively. The measurement controller 114 controls the optical path and wavelengths of the probe light 8e and the exciting light 111 as well as the intermittent intervals of the exciting light 111 by the chopper 112, and also calculates light absorption characteristics by the signal from the lock-in amplifier 109.

The liquid tank 101 is not necessarily made transparent as a whole, only if transparent windows are provided at the portions for optical path of the probe light 8e and the exciting light 111. The liquid 102 will have no great influence on measurement, if it absorbs little of the exciting light 111, although the probe light 8e may be more or less directly influenced thereby, but it is preferably transparent. In FIG. 16, only the optical control system and the liquid tank portion are shown, and film forming portion and the surface pressure controlling portion are omitted.

The operation is to be explained below. First, the exciting light 111 emitted from the excitation light source 110 is modulated into intermittent light by the chopper 112 and irradiates the measuring site of the thin film 104 spread on the liquid surface 103 in the liquid tank 101 from below the liquid surface 103. In this irradiation, the exciting light 111 is introduced at an incident angle greater than the critical angle of the liquid 102 to be totally reflected at the liquid surface 103, passes through the liquid 102 and comes out of the liquid tank 101. To the gas phase above the liquid surface 103, only a very slight quantity of light of shorter wavelengths penetrates out as evanescent wave during the total reflection. The exciting light 111 coming out from the liquid tank 101 is absorbed by the absorber 113 to cut unnecessary light. In the region above the measuring site at which the intermittent exciting light 111 is totally reflected, the thin film 104 on the liquid surface 103 absorbs the light and generates intermittently heat by a radiation-less relaxation process, whereby refractive index change in the vicinity will intermittently occur.

On the other hand, the probe light 8e emitted from the probe light source 7 passes directly below the liquid surface 103 in parallel to the liquid surface 103 and therefore passes through the region at which the refractive index is intermittently changed by irradiation of the above exciting light 111. When the above prove light 8e passes nearby the measuring site at which such an intermittent change of refractive index occurs, the optical path is deflected as shown by the dotted line corresponding to the refractive index distribution changed and detected at the PSD light receiving surface of the light position detector 107.

At this time, even if the beam of the probe light may be fluctuated in minute amount by the fluctuation of the probe light source 7 for probe, as described above, the beams are respectively shifted in the directions symmetric to each other with the position corresponding to the deflection degree by absorption of the sample when there is no light source fluctuation as the center, whereby the output becomes the constant value corresponding to absorption of the sample from the measuring principle of PSD, thus cancelling the influence of fluctuation of the light source for probe.

Thus, the liqht position detector 107 receives continuously the probe light 8e and sends a signal regarding the light receiving position of the probe light 8e through the driver 108 to the rock-in amplifier 109. The lock-in amplifier 109 receives the signal from the detector 107 simultaneously with receiving the signal from the chopper 112 and, by synchronizing both signals, the light receiving position signal of the probe light 8e during irradiation of the exciting light 111 and the light receiving position signal of the probe light 8e during non-irradiation of the exciting light 111 are sent to the measurement controller 114 as separated with good S/N ratio. The measurement controller 114 determines the deflection of the probe light 8e with respect to the wavelength of the exciting light 111 at that time based on the signal sent and calculates light absorption characteristics based on the measured value. Also, when similar measurements are carried out by successively changing the wavelength of the exciting light 111, spectral absorption characteristics of the thin film 104 can be obtained.

During this measurement, the measuring site can be freely selected by controlling the optical path of the exciting light 111 by the measurement controller 114 and also the optical path of the probe light 8e can be controlled by the measurement controller 114 depending on the position of the liquid surface 103 in order to conduct accurate measurement. Further, the operations can be simplified by carrying out necessary controls of the probe light source 7, the excitation light source 110 and the chopper 112 automatically all by the measurement controller 114.

The light energy absorbed by the thin film 104 can be determined from the dose distribution at the measuring site of the exciting light 111, the characteristic of the refractive index change by the heat of the liquid 102, the incident beam position of the probe light 8e and deflection at that time. Accordingly, if the irradiated energy of the exciting light 111 on the thin film 104 is monitored by a photosenser or the like, the absolute light absorption characteristic of the thin film 104 can be obtained from both. And, by changing the wavelength of the exciting light 111, the absolute spectral absorption characteristic can be obtained. Further, only by determining previously the relative strength of the exciting light 111 at respective wavelength and determining the deflection of the probe light 8e corresponding to the wavelength, relative spectral absorption characteristics can be obtained. The relative value and the absolute value of the light absorption characteristic may be selected suitably depending on the purpose of measurement.

Figure 17:
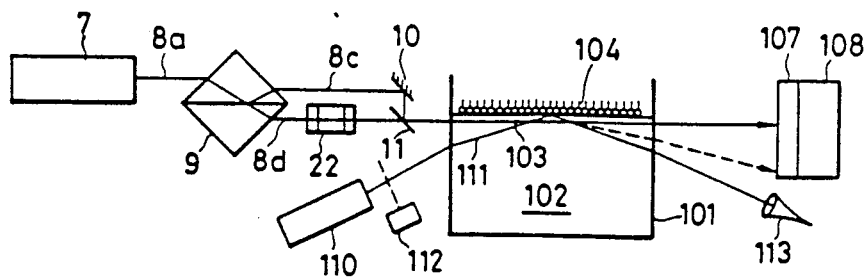

FIG. 17 is a schematic illustration of a second embodiment of the film forming device according to the present invention. This embodiment concerns the case of measuring the deflection of the probe light in any direction according to the two dimensional PSD. It is constituted such that an image rotator 22 is arranged between the beam splitter 9 and the half mirror 11, and one of the probe light beams 8d splitted by the beam splitter 9 is reversed in the upper and lower passing positions in the direction perpendicular to the splitting direction of the beam splitter. Other constitutions are the same as FIG. 16.

The image rotator 22 may be placed in either of the optical paths for the probe light beams 8c, 8d split by the beam splitter 9.

Figures 18A, 18B:
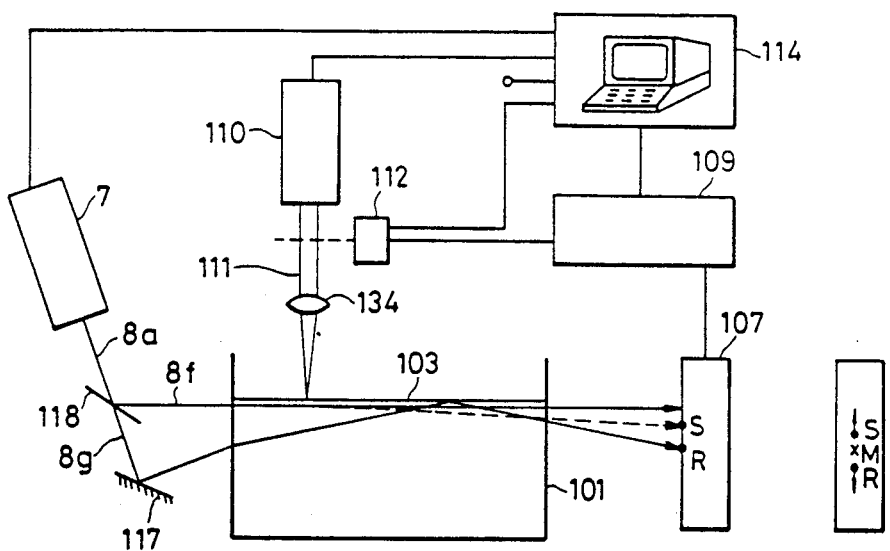

FIG. 18A is a schematic illustration of a third embodiment of the film forming device according to the present invention, showing the case when measuring according to one-dimensional PSD. In any of the embodiments as described above, the exciting light is permitted to be incident from below the liquid surface, but in this embodiment, the excited light is permitted to enter from above the liquid surface.

In FIG. 18A, the probe light beam 8a emitted from the probe light source 7 is separated by the half mirror 118 into the two light beams 8f, 8g, of which 8f is irradiated as the probe light directly below the liquid surface 103 in parallel to the liquid surface 103 and goes toward the PSD light receiving surface of the light position detector 107. On the other hand, 8g is reflected against the mirror 117 as the reference light, totally reflected against the liquid surface 103 of the reference region on which the excited light 111 is not irradiated and goes similarly toward the PSD light receiving surface of the light position detector. On the position S and 8g at the position R, respectively.

Figure 18C:
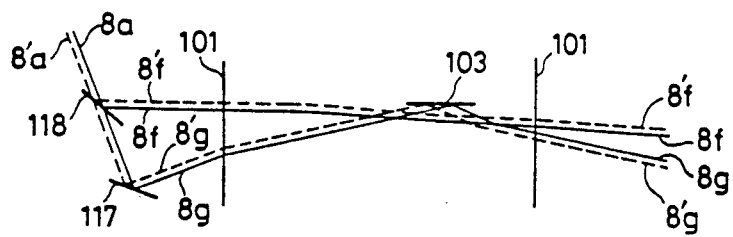

When the beam moves from 8a to 8a' as shown in FIG. 18C by the fluctuation in the probe light source, the beam irradiated positions move in the directions opposite to each other on the PSD light receiving surface in the directions of the arrowheads shown in FIG. 18B. The optical paths are shown by the broken lines in FIG. 18C. When such a fluctuation has occured, the output of PSD always represents the constant position of the center position (M in the drawing) from the measuring principle, provided that the doses at S and R are equal, whereby the influence by light source fluctuation can be cancelled.

Figures 19A, 19D:
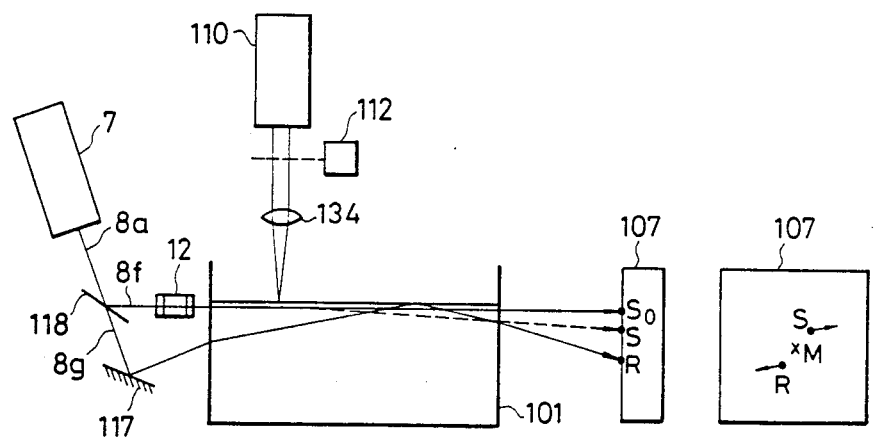

FIG. 19A is a schematic illustration of a fourth embodiment of the film forming device according to the present invention. This embodiment concerns the case when measuring the deflection two-dimensionally by replacement of the one-dimensional PSD used in the above embodiment of FIG. 18 with a two-dimensional PSD, and it is constituted such that an image rotator 12 is placed after the light beam 8f so as to rotate the beam in the direction perpendicular to the paper surface. Other constitutions are entirely the same as in FIG. 16.

Figure 19B:
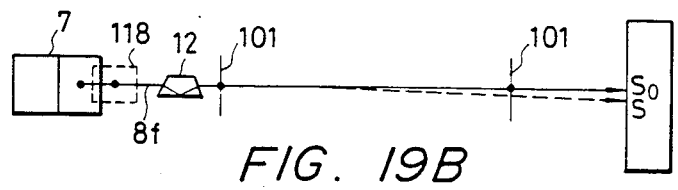
Figure 19C:
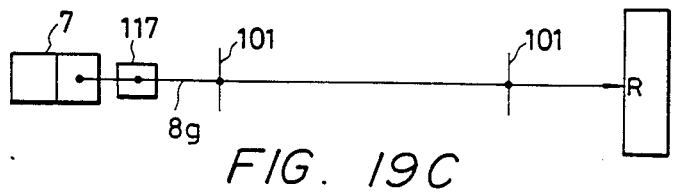
Figure 20A:
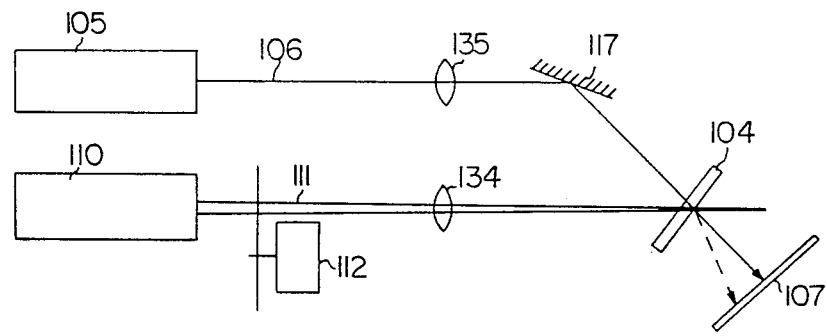
FIGS. 20A and 20B are schematic illustrations of the PDS device of the prior art.
Figure 20B:
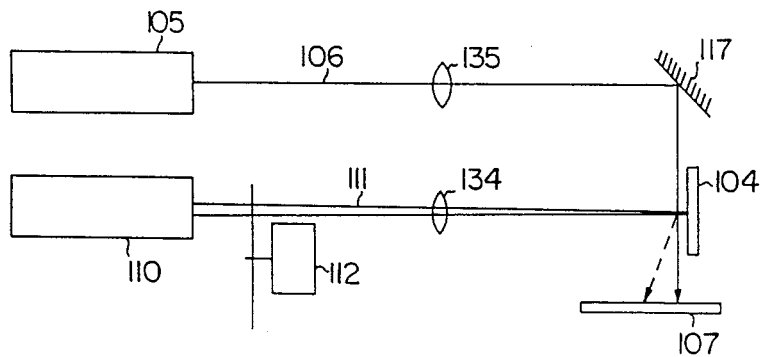
Figure 21:
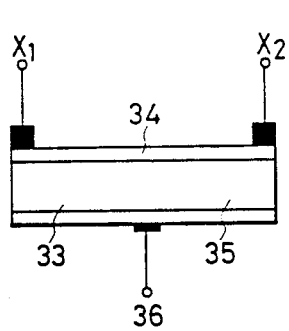
FIG. 21 and FIG. 22 are schematic illustrations of constitution of PSD.
Figure 22:
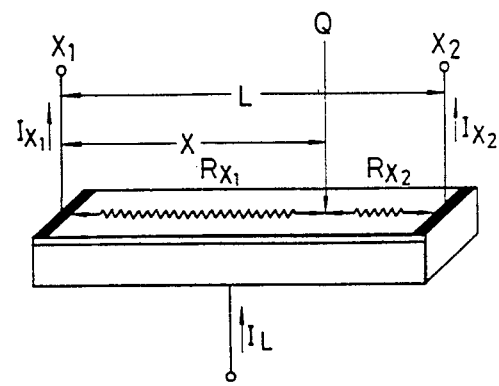
Figure 23:
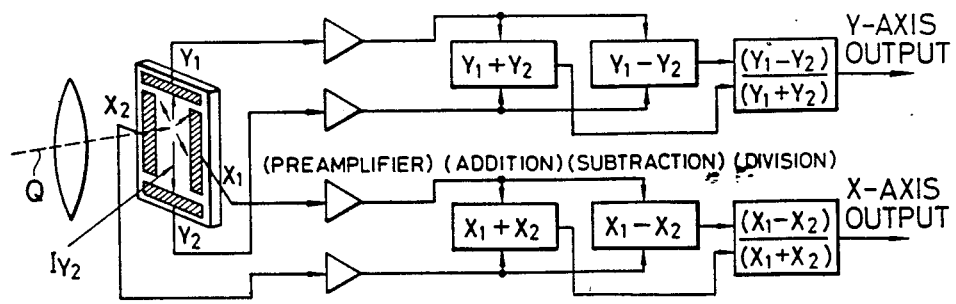
FIG. 23 is the diagram showing its actuation principle.
Figure 24:
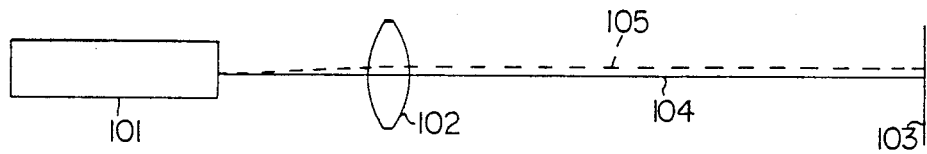
FIG. 24 is a schematic illustration showing one example of light irradiation device of the prior art.

FIGS. 19B and 19C are side views of the measuring system shown in the same FIG. 19A. FIG. 19B shows the optical path 8f and FIG. 19C shows the optical path 8g. The positions on the PSD light receiving surface in this case are shown in FIG. 19D. If 8f is irradiated at the position shown by S and 8g at the position shown by R. S and R will move in the directions of the arrowheads by deviation of 8a due to light source fluctuation, but the center position M of their average will not change, whereby the output from PSD becomes always constant to cancel the influence from light source fluctuation.

As described above, according to the present invention, there can be provided a high precision light beam fluctuation compensating device which is capable of compensating the deviation of light beam due to fluctuation of light source, thereby making the center of the irradiated beam intensity on the target surface always constant.

Further by use of the above device, the measurement precision can be improved to the limit of the resolving power inherent in PSD and therefore an optical device equipped with such a device can be used for measurement of light absorption characteristics not only of various conventional gaseous, liquid and solid samples but also of a sample under special environment such as an LB film (thin film) with high precision and at high sensitivity.

We claim:

1. A device for measuring light absorption characteristics of a thin film spread on a liquid surface, comprising
   a liquid tank for containing liquid therein, with a thin film for a sample being formed on the surface of the liquid;
   an excitation light source for emitting excitation light;
   a light intensity modulator for modulating the intensity of the excitation light provided before a measuring site;
   a probe light source emitting a light beam;
   a light position detector for receiving the light beam;
   light splitting means for splitting the light beam emitted from said probe light source into two light beams; and
   a first optical system for projecting each of the two light beams through a measurement site of the sample onto said light position detecting surface, said light splitting means and said first optical system being provided for steadily maintaining the intensity center of the light beam projected onto a detecting surface of said light position detector at an invariable position without positional fluctuation independently of fluctuation of an emitting angle to the thin film of said probe light source.

2. The device according to claim 1, wherein said liquid tank is capable of containing a monomolecular film as the thin film.

3. A device for measuring light absorption characteristics of a thin film spread on a liquid surface, comprising
   a liquid tank for containing liquid therein, with a thin film for a sample being formed on the surface of the liquid;
   an excitation light source for emitting excitation light;
   a light intensity modulator for modulating the intensity of the excitation light provided before a measuring site;
   a probe light source emitting a light beam;
   a light position detector for receiving the light beam;
   light splitting means for splitting the light beam emitted from said probe light source into two light beams;
   a first optical system for projecting each of the two light beams through a measurement site of the sample onto said light position detecting surface; and
   a second optical system provided in the path of at least one of the two light beams between said light splitting means and said first optical system, said light splitting means, said first optical system and said second optical system being provided for steadily maintaining the intensity center of the light beam projected onto a detecting surface of said light position detector at an invariable position in any direction relative to X-Y coordinates on the surface without positional fluctuation independently of fluctuation of an emitting angle to the thin film of said probe light source.

4. The device according to claim 3, wherein said liquid tank is capable of containing a monomolecular film as the thin film.

* * * * *

UNITED STATES PATENT AND TRADEMARK OFFICE
CERTIFICATE OF CORRECTION

PATENT NO. : 4,952,027

DATED : August 28, 1990

INVENTOR(S) : Kenji Saito, et al.

It is certified that error appears in the above-identified patent and that said Letters Patent is hereby corrected as shown below:

On title page, item

[56] REFERENCES CITED:

"Absortion" should read --Absorption--.

COLUMN 2:

Line 29, "propotional" should read --proportional--.

COLUMN 3:

Line 6, "$I_{x2}I_L \cdot X/L$" should read --$I_{x2} = I_L \cdot X/L$--.

COLUMN 8:

Line 46, "134" should read --135--.

COLUMN 9:

Line 4, "d*vice" should read --device--.

Line 46, "type PSD." should read --type PDS.--.

COLUMN 10:

Line 39, "rock-in" should read --lock-in--.

UNITED STATES PATENT AND TRADEMARK OFFICE
CERTIFICATE OF CORRECTION

PATENT NO.  : 4,952,027

DATED       : August 28, 1990

INVENTOR(S) : Kenji Saito, et al.

It is certified that error appears in the above-identified patent and that said Letters Patent is hereby corrected as shown below:

COLUMN 11:

Line 44, "rock-in" should read --lock-in--.

COLUMN 12:

Line 59, "detector. On" should read --detector on--.

Signed and Sealed this

Thirtieth Day of March, 1993

Attest:

STEPHEN G. KUNIN

*Attesting Officer*   Acting Commissioner of Patents and Trademarks